United States Patent
Sanchez Ramos et al.

(10) Patent No.: US 10,288,786 B2
(45) Date of Patent: May 14, 2019

(54) DEVICE AND METHOD FOR DETECTION AND QUANTIFICATION OF THE VARIATION OF EYE DAMAGE CAUSED BY THE BLUE AND VIOLET LIGHT OF THE VISIBLE SPECTRUM

(71) Applicants: UNIVERSIDAD COMPLUTENSE DE MADRID, Madrid (ES); CRAMBO, S.A., Torrejón de Ardoz, Madrid (ES)

(72) Inventors: Celia Sanchez Ramos, Madrid (ES); Nilo Garcia Manchado, Madrid (ES)

(73) Assignees: UNIVERSIDAD COMPLUTENSE DE MADRID, Madrid (ES); CRAMBO, S.A., Torrejón de Ardoz, Madrid (ES)

( * ) Notice: Subject to any disclaimer, the term of this patent is extended or adjusted under 35 U.S.C. 154(b) by 0 days.

(21) Appl. No.: 14/654,813

(22) PCT Filed: Jul. 5, 2013

(86) PCT No.: PCT/ES2013/070476
§ 371 (c)(1),
(2) Date: Jun. 22, 2015

(87) PCT Pub. No.: WO2014/096477
PCT Pub. Date: Jun. 26, 2014

(65) Prior Publication Data
US 2015/0342457 A1 Dec. 3, 2015

(30) Foreign Application Priority Data
Dec. 21, 2012 (ES) .................................. 201201268

(51) Int. Cl.
*A61B 5/00* (2006.01)
*G02B 5/22* (2006.01)
(Continued)

(52) U.S. Cl.
CPC .............. *G02B 5/22* (2013.01); *A61B 3/1025* (2013.01); *A61B 5/0022* (2013.01); *A61B 5/68* (2013.01);
(Continued)

(58) Field of Classification Search
CPC .. G02B 5/23; G02B 5/223; G02B 5/22; G09F 9/33; H01L 33/00; G02C 7/104;
(Continued)

(56) References Cited

U.S. PATENT DOCUMENTS 5,047,447 A 9/1991 Gallas
2006/0092407 A1 5/2006 Tan et al.
(Continued)

FOREIGN PATENT DOCUMENTS

WO WO 90/05321 A1 5/1990
WO WO 2008/116333 A1 10/2008
WO WO 2010/143089 A1 12/2010

OTHER PUBLICATIONS

Definition of quantum/quanta from Google search dated Feb. 14, 2017.*
(Continued)

*Primary Examiner* — Elmer M Chao
(74) *Attorney, Agent, or Firm* — Arent Fox LLP (57) ABSTRACT

Method, device (100) and system (200) for detection and quantification of the variation of eye damage caused by the blue and violet light of the visible spectrum comprising the steps of detecting the incident radiation on an individual's visual system; calculating the incident radiation within the range between 380 and 500 nm; establishing at least one threshold of incident radiation within said range; detecting if at least one threshold established for said range has been exceeded; warning of the excess of at least one threshold; measuring the exposure time to incident radiation; and
(Continued)

inferring in the different ocular structures of an individual the effect of incident radiation and warning of such effect.

24 Claims, 4 Drawing Sheets (51) Int. Cl.
| | |
|---|---|
| *A61B 3/10* | (2006.01) |
| *H04N 9/64* | (2006.01) |
| *G02B 19/00* | (2006.01) |
| *G01J 1/02* | (2006.01) |
| *G01J 1/42* | (2006.01) |
| *A61B 5/0205* | (2006.01) |
| *A61B 5/024* | (2006.01) |
| *A61B 5/11* | (2006.01) |
| *H01L 33/44* | (2010.01) |
| *G02B 5/20* | (2006.01) |

(52) U.S. Cl.
CPC ........... *G01J 1/0219* (2013.01); *G01J 1/0233* (2013.01); *G01J 1/4204* (2013.01); *G01J 1/429* (2013.01); *G02B 5/223* (2013.01); *G02B 19/0066* (2013.01); *H04N 9/64* (2013.01); *A61B 5/0075* (2013.01); *A61B 5/0205* (2013.01); *A61B 5/02416* (2013.01); *A61B 5/1118* (2013.01); *A61B 5/4857* (2013.01); *A61B 5/681* (2013.01); *G02B 5/201* (2013.01); *H01L 33/44* (2013.01)

(58) Field of Classification Search
CPC ......... G09G 2320/0666; G09G 3/3406; G09G 3/3413; A61B 5/0075; A61B 5/681; A61B 5/4857; A61B 5/0205; A61B 5/1118; A61B 5/02416; A61B 5/68
See application file for complete search history.

(56) References Cited

U.S. PATENT DOCUMENTS

| | | |
|---|---|---|
| 2008/0221674 A1 | 9/2008 | Blum et al. |
| 2009/0166508 A1 | 7/2009 | Huang et al. |
| 2010/0102283 A1 | 4/2010 | Royster, Jr. et al. |
| 2010/0127159 A1 | 5/2010 | Watanabe |
| 2010/0282266 A1 | 11/2010 | Sanchez Ramos |
| 2014/0058192 A1* | 2/2014 | van Rijn ............... A61M 21/00 600/26 |
| 2015/0041663 A1* | 2/2015 | Oliver ................... G01J 1/0219 250/372 |

OTHER PUBLICATIONS

International Search Report for PCT/ES2013/070476 dated Dec. 20, 2013.
Ueda., et al., "Eye damage control by reduced blue illumination," Experimental Eye Research, 2009, vol. 89, n° 6, pp. 863-868.
Wu, et al., "Photochemical damage of the retina," Survey of Ophthalmology, Sep.-Oct. 2006, vol. 51, n° 5, pp. 461-481.
Supplementary European Search Report issued in European Patent Application No. 13864609 dated Oct. 20, 2016.

* cited by examiner

DEVICE AND METHOD FOR DETECTION AND QUANTIFICATION OF THE VARIATION OF EYE DAMAGE CAUSED BY THE BLUE AND VIOLET LIGHT OF THE VISIBLE SPECTRUM

CROSS-REFERENCE TO RELATED APPLICATIONS

This application is a National Stage entry of International Application No. PCT/ES2013/070476, filed Jul. 5, 2013, which claims priority to Spanish Patent Application No. P201201268 filed Dec. 21, 2012. The disclosures of the prior applications are hereby incorporated in their entirety by reference.

FIELD OF THE INVENTION

The object of the present invention is a device and method for detection and quantification of the variation of eye damage caused by the blue and violet light on the visible spectrum, i.e., the electromagnetic radiation between the wavelengths of 380 nm to 500 nm for any light emission source, from natural or artificial light, to that from emitters like screens based on LED technology.

STATE OF THE ART

The electromagnetic spectrum (EME) is the energy distribution of the whole of the electromagnetic waves that a substance emits (emission spectrum) or absorbs (absorption spectrum). The EME includes a wide range of radiation, from that of lower wavelength such as gamma rays and x-rays, passing through ultraviolet radiation, light and infrared rays, to the electromagnetic waves with longer wavelength, such as radio waves.

The light spectrum is the region of the electromagnetic spectrum that human eye is able to perceive. Electromagnetic radiation in this range of wavelengths is also called 'visible' or simply light. There are no exact limits in the visible spectrum; a typical human eye responds to wavelengths from 380 nm to 780 nm, although the eye adapted to the dark can see over a greater range, ranging from 360 nm to 830 nm.

The retina auto-protects itself from the short wavelengths in several ways: with a heterogeneous distribution of the photo-receptors in such a way that photo-receptors, sensitive to the short wavelengths, do not exist in the macular depression and by the action of yellow pigments (lutein, zeaxanthin and meso-zeaxanthin) existing in the same area that also perform a protective action. In addition, the crystalline increases its proportion of yellow chromophores with age.

These natural protections of the human eye against the shortest wavelengths (the crystalline and those of the retina) can find themselves seriously affected by certain pathologies and/or surgical interventions and even over time.

Some techniques have been developed to protect healthy eyes, cataract operated eyes, and eyes in neuro-degenerative process from short wavelengths:

Supplement, the deficit of the human eye as a therapeutic and preventive measure to replace and/or improve the natural protection by selective, reflective and interference absorbance filters.

Since the middle of the 90's, intraocular lenses provided with a yellow filter have been implanted on cataract operated eyes. This alternative involves a surgical procedure with all its obvious risks and difficulties. There also exists a large number of people operated from cataracts to which a transparent intraocular lens has been implanted to substitute the inner substance of the crystalline that does not have the necessary yellow pigmentation protection. In these cases, it is necessary to complement the artificial crystalline, which is exempt of yellow pigmentation, with the insertion of a yellow pigmentation support system that is absorbent or blocking of the short wavelength.

A blocking element of the short wavelengths is a device designed to separate, pass or delete a group of objects or things of the total mixture. The blocking elements are designed for the selection of a particular range of wavelengths of light. The mechanism consists of the blocking of wavelengths, allowing the passage of other wavelengths.

There are different types of filters applied to the human eye on the market. For instance, the patent application WO 98/44380 describes a filter applied in a contact lens that does not cover the whole of said contact lens, understanding the whole as iris area, pupil area and the contact lens body, this fact being fundamental for avoiding irregularities in vision. On the other hand, the document WO 91/04717 describes intraocular lenses for treating of Age-Related Macular Degeneration (AMD) which is not the object of the present invention. It is also known the fact of using yellow filters in ophthalmic lenses, for example through the document GB 1 480 492.

The yellow filter can be used in multiple applications, as shown by the documents located in the current state of the art. Thus, the document DE 358 948 describes a yellow filter applied to an electrical lighting device, but combined with a second red-colored filter, which moves away from the inventive concept described in the present invention.

The document ES 1 046 793 U describes an external support device of different lighting filters, with different colors, which moves away from the inventive concept of the present invention which lies in a unique blocking element of short wavelengths, integrated in a given material, to eliminate the short wavelengths from the visible light spectrum before it reaches the user due to pernicious effects produced by the high energy of this light range, aim that, evidently, is not achieved with this document.

The document WO 90/05321 describes a filter with a series of technical features but that absolutely defines a pathophysiological application and in addition, the filter described in the patent application WO 90/05321 is not homogeneous in its absorbance, and may produce unwanted effects.

Dr. Celia Sanchez-Ramos is the inventor of the patents ES2247946, ES2257976, ES2281301, ES2281303, ES2289957, ES2296552, ES2298089, ES2303484 and ES2312284. However, although these documents are referred to the issue of damage caused by ambient light, especially the short wavelengths on the spectrum from 380 to 500 nm, none of these documents explains the problem derived from the mass and daily use of screens primarily based on LED technology in its different variants, like OLED, LCD-LED, AMOLED, among other cutting-edge technologies for smartphones, electronic tablets, laptops and televisions, projectors and in general any screen with LED technology and/or LED backlight.

It is clear that today any particular user spends an average of 4-8 hours a day, or more, in front of LED-type displays, i.e. receiving an emission of short wavelengths at a usually very small distance (on the order of 30-50 cm), which has a significant negative impact on the eye and human vision. This problem is described in the state of the art in [Behar- Cohen et al. '*Light-emitting diodes (LED) for domestic lighting: Any risks for the eye?' Progress in Retinal and Eye Research* 30 (2011)239-257].

Another document that describes the associated problems in [Cajochen et al. '*Evening exposure to a light-emitting diodes (LED)—backlight computer screen affects circadian physiology and cognitive performance*', *Journal of Applied Physiology* 110: 1432-1438, 2011, first published 17 Mar. 2011] where the need to adapt the light emission to the sleep cycle is described.

Said documents, in the conclusions thereof, express the convenience of assessing the potential toxicity of the light emitted by the LEDs, depending on the various devices available on the market so that efficient recommendations can be made to the domestic light manufacturers, due to the increased presence of LED-type lighting for indoor environments. However, this document does not commit to a solution to combine the evolution of the LED technique with a risk-free everyday use. That is, this document advocates, directly, the limitation and legal regulation of light emissions, without proposing any kind of solution for the already marketed products.

However none of the known documents express the need to have a device and/or a method to detect and quantify these harmful emission of blue light on the visible spectrum so that it is possible to alert the user of a possible excessive exposure to these emissions.

On the other hand, damage of blue light are described in the document ['*Effects of light-emitting diode radiations on human retinal pigment epitelial cells in vitro*, C. Sánchez-Ramos et al. *Photochem Photobiol* 2013 March-April; 89(2) 467-73, doi: 10.1111/j.1751-1097.2012.01237.x] where the damage caused by the emissions of the LEDs on the screens commonly used in televisions, mobile phones and personal computers are analyzed.

It is imperative, therefore, the need for a system that allows the detection and quantification of the presence of blue light, warning the user of the possible risks to which is exposed by the continued use of these emission sources.

There are no known devices for warning of emissions in the range of 380-500 nm and, especially, devices that alert and quantify the damage to the ocular system. However, documents relating to the detection of UV emissions are known such as EP 1 441 208, the document GB 2 419 665, the document GB 2 427 464 and y US 2009/0135003.

DESCRIPTION OF THE INVENTION

To solve the technical problem indicated, the present invention describes, in a first aspect, a method for detection and quantification of blue and violet light from the visible spectrum comprising the steps of detecting the emission of a light source; calculating emissions in the range of 380-500 nm which contains the light; establishing a maximum emission threshold in said range; detecting whether the threshold set for this range has been exceeded; calculating the exposure time to the emission of the light source; and warning of the excess of the mentioned threshold.

This threshold may depend on each person. That is, it can be a generic threshold or one defined for each person.

In a second aspect of the invention, the method described is implemented in a portable electronic device for detection and quantification of the blue and violet light band of the visible spectrum comprising a light detector in the range of the visible spectrum; a signal conditioning circuit connected to the detector; an analog-to-digital converter; a processor; and a program that is stored in the memory of the processor and that it is configured to run by the processor, the program including instructions for running the method described.

In a third aspect of the invention, the method is implemented in a computer system comprising a screen connected to a screen controller; a program memory; a camera; a processor; and a program that is stored in the memory of the processor and that it is configured to run by the processor, the program including instructions for selecting the type of screen; establishing the emission power of the screen and running the method described.

Finally, in a fourth aspect of the invention is claimed the computer program product that contains the instructions to execute the method.

Throughout the description and claims, the word 'comprises' and its variations are not intended to exclude other technical features, additives, components or steps. For those skilled in the art, other objects, advantages and characteristics of the invention will emerge in part from the description and in part from the practice of the invention. The following examples and drawings are provided by way of illustration, and are not intended to be limiting of the present invention. Furthermore, the present invention covers all the possible combinations of particular and preferred embodiments herein indicated.

BRIEF DESCRIPTION OF THE DRAWINGS

Described very briefly hereinafter are a series of drawings that help to better understand the invention and which are expressly related to an embodiment of said invention that is presented as a non-limiting example thereof.

DETAILED DESCRIPTION OF THE INVENTION AND EXAMPLE

Figure 1A:
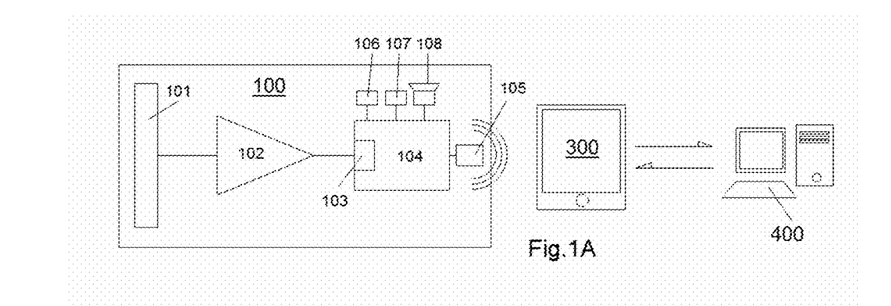
FIG. 1 schematically shows a portable electronic device (100) and a computer system (200) that implement the method for detection and quantification of blue light on the visible spectrum.

FIG. 1 shows the different practical embodiments of the invention. FIG. 1A shows a portable electronic device 100 which is logically transportable by the user in a position such that allows the reading of the incident light thereon.

The portable device comprises a visible light detector 101, like LDR, CMOS sensors, CCD sensors, photodiodes, solar cells and in general, any visible light detector that is connected to a signal conditioning circuit 102 that filters and adapts the signal emitted by detector 101 for its subsequent digital analogue conversion A/D 103. The digitized signal passes to a processor 104 which comprises in an internal memory (although it could be implemented in a memory external to the processor 104) a program consisting of instructions which, executed by the processor 104, are configured to detect the emission of a light source, i.e., to establish the presence of blue light on the visible spectrum.

Once the light on the visible spectrum is detected, the processor 104 is configured to calculate the amount of emissions in the range of short wavelengths between 380-500 nm. This could be, for example, by selecting a photodiode with a response in that range as detector 101, such that by conditioning the signal and evaluating its intensity on the processor 104, that amount of emissions (greater signal, greater presence of blue) could be set. This signal would then compare with a value predefined for that range of emissions, so that if there is an emission above the cited threshold value, exposure to blue light, i.e. to the spectrum between 380-500 nm, is understood as harmful to the visual health of the subject.

The processor 104 also calculates the time during which the subject is exposed, such that it allows warning the user (the subject) in various ways, such as for example, a Bluetooth signal 105 to his/her mobile phone 300. In addition, the mobile phone has the ability to connect to an external server 400 and assess the exposure, store it, or create a record of harmful actions with which then warn to or prevent the future user.

Similarly, the device 100 itself comprises a signal light, which in the embodiment shown in FIG. 1 comprises a red LED 106 and a green LED 107 to perform said warning where logically the LED red 106 will light when the permitted emission threshold is exceeded. In addition, an acoustic signal 108 may be incorporated.

Figure 1B:
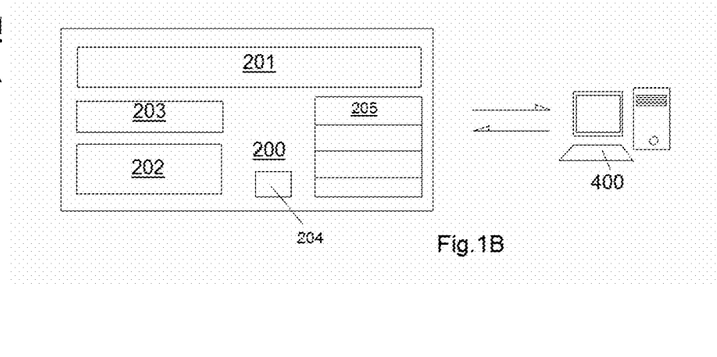

The device object of the present invention in another embodiment may be integrated into a computer system, as shown in FIG. 1b, in such a way that it is possible to measure the emissions at the source, i.e., at the emission source itself, such as a LED-type screen or other equivalent. By computer system has to be understood any programmable device that contains a light-emitting screen on the visible spectrum, such as a laptop, a tablet, a next-generation mobile, a desktop computer or a television configured to that end.

Thus, the computer system comprises 200 comprises a screen 201 connected to a controller which in turn is connected to at least one processor 202, a program memory 203 and a camera 204, such that the programs 205 stored in the memory 203 are configured to be executed by the processor (202), the program or programs (205) including instructions to select the type of screen (201) and establish the emission power of the screen (201), that is related to, for example, the brightness of the screen 201.

After that, the emissions in the range of the 380-500 nm containing the light emission, for example, through the characterization of the type of screen 201 stored in the memory 203 and previously selected, are calculated. Subsequently, a maximum emission threshold in said range is set, and whether the threshold set for that range has been exceeded is detected, calculating the exposure time to the emission of the light source and warning of overcoming of above-mentioned threshold. In addition, an external server 400 may be connected and assess the exposure, store it, or create a record of harmful actions with which then warn to or prevent the future user.

The object of the present invention, as already widely indicated, is to infer and assess the eye damage by light exposure, i.e. that the described device must be able to measure, evaluate and warning of the amount of emissions in the range of 380-500 nm to which the user is exposed. To do so, first, it must be set the presence of intrinsic and extrinsic factors affecting the quantification of the variation of eye damage.

Logically, a first factor to be considered is the ambient lighting, which is detected by the device itself through the detector 101, or is established as an independent factor that weights this signal. It should be noted that the ambient light depends directly on the position of the user and the time of day, so incorporating a GPS circuit to the device is possible to know:

i. Position
ii. Climatology
iii. Time of day

Thus, if the user is, for example, in the Pyrenees in December, some climatic conditions are assumed, such as snow, which weights the extent of emissions, in the same way that we know the height, since it is not the same type of emission at 2000 meters as at sea level, and the time of day, since in the Middle hours, and depending on the position, the emissions received vary.

A second factor to be considered is the emitting device viewed by the user, including the size of the same, the estimated distance to which observes it, the emission intensity (i.e. brightness) and if it implements or not a filter for emissions on the spectrum between 380 and 500 nanometers.

In a practical embodiment of the invention, the device 100 comprises, stored in a memory, different types of displays selectable by the user, such that the user selects the data from emission source. In other embodiments, the detection is automatic, for example, if the invention is implemented on a mobile phone, a television or other emission sources, in such a way that the emissions from each source are sent to, for example, the computer system 200 acting as the network master, or the user's telephone with the same function. Therefore, in another practical embodiment of the invention, different emission sources present in a house or office for a user or users can establish a communications network to exchange information between them of emissions and exposure time, enabling the sum of these data for a particular user and, logically, improving the quality of quantification and inference of ocular damage for a particular user.

On the other hand, it must be taken into account a number of factors directly related to the user, such as age, disease states (for example, glaucoma and/or retinopathy), the hours of activity, type of eye activity, the refractive state, i.e. if he/she is near-sighted, far-sighted, astigmatic, and/or has presbyopia or other ocular anomalies, as well as if he/she has any color conditions.

Within the type of ocular activity can be differentiated both habits of life and, for example, the profession and the status of concentration of the user for each activity. Life habits influence since the level of exposure at which a fisherman is subjected is not the same as that of a welder or a waiter, since certain conditions will be assumed, such as the reflection of the water and the hours at work in the case of fishermen, therefore it is a factor that is weighted at the rate of quantification of eye damage.

On the other hand, the state of concentration of the user is relevant, since it is shown that greater concentration, the blinking of the user is less and, as a result, the emission received directly by the ocular system increases. In addition, the type and time of the user's refresh is different.

Therefore, the device 100 is customizable by the user, or may be customized at the factory for a particular user by integrating its specific characteristics.

The following table set forth, by way of example, and not as a limitation, a series of factors with a maximum and minimum percentage to precisely set the maximum and minimum absorbance that a protection filter should have in that wavelength range.

TABLE 1

| Factor | Degree | Maximum limit (%) | Minimum limit (%) |
|---|---|---|---|
| Age (years) | 0-10 | 10 | 2 |
| | 10-20 | 8 | 2 |
| | 20-40 | 5 | 2 |
| | 40-60 | 7 | 4 |
| | 60-75 | 10 | 8 |
| | >75 | 12 | 8 |
| Type of used devices (working distance) | Smartphones (25-40 cm) | 2 | 1 |
| | Tablets (25-40 cm) | 3 | 1 |
| | Computer screens (41-70 cm) | 4 | 2 |
| | Television screens (>70 cm) | 4 | 2 |
| Total exposure time (hours) | <3 | 2 | 1 |
| | 3-5 | 3 | 2 |
| | 5-8 | 4 | 3 |
| | 8-10 | 5 | 3 |
| | >10 | 5 | 3 |
| Conditions of lowest ambient lighting during the use of the devices (cd/m²) | Photopic (>5) | 2 | 1 |
| | Mesopic (0.005-5) | 5 | 2 |
| | Scotopic (<0.005) | 10 | 4 |
| Retinal disease states | | | |
| Disease State | Mild stage | 50 | 30 |
| | Moderate stage | 60 | 40 |
| | Severe stage | 70 | 50 |
| Corneal disease states | | | |
| | Mild stage | 20 | 10 |
| | Moderate stage | 30 | 20 |
| | Severe stage | 40 | 30 |
| | Palpebral disease states | 5 | 2 |
| | Conjunctival disease states | 5 | 2 |
| | Scleral disease states | 5 | 2 |
| | Glaucoma | 20 | 10 |
| | Pseudophakic/Aphakia | 30 | 10 |

Figure 2A:
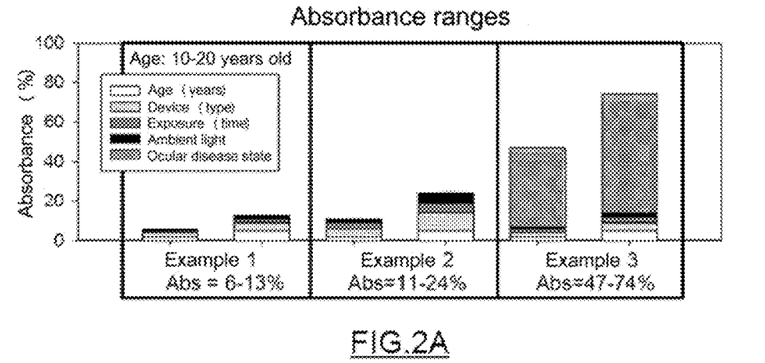
FIG. 2 shows the selective absorbance of the blocking element of short wavelengths of the present invention for three examples of people of different age: 25 years old (FIG. 2*a*), 45 years old (FIG. 2*b*) and 76 years old (FIG. 2*c*).
Figure 2C:
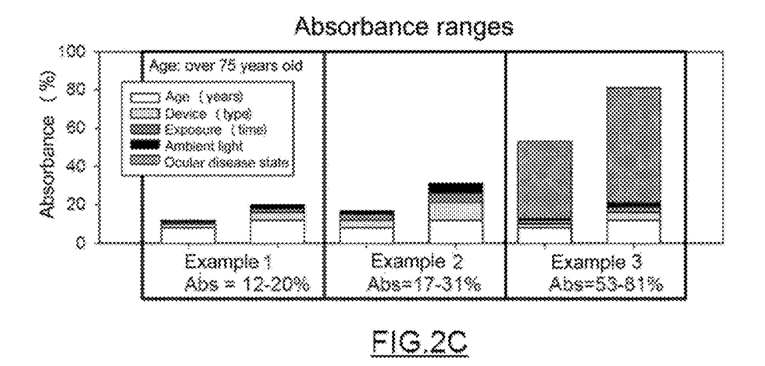

The sum of the various factors listed by way of example in table 1 is what gives as a result a maximum and minimum absorbance threshold corresponding to FIG. 2, where, by way of an example, for a user between 25 years old (max. 5, min. 2) that works with a computer (4/2), with an exposure time to the light source by the user less than 3 hours (2/1), with an ambient lighting of the place where the user interacts with the photopic LED-type light source (2/1) and without disease states, is stated that we would have a maximum absorbance in the range of 380-500 nm of (5+2+2+2) of 13%, while the minimum of absorbance would be 6%, as shown, for example in FIG. 2 (example 1). However, if the same individual uses various electronic devices (computer, tablet and smartphone) for more than 10 hours in environments of high and low lighting, the preferred absorbance range would be between 11-24% (example 2). On the other hand, if the individual has a moderate retinal disease state and was exposed to television for 3-5 hours a day in high light conditions, the recommended absorbance range would be 47-74% (example 3).

Therefore, the inverse of that value is what can be set as weight $k_i$ (although other equivalent might be defined) for each accelerator factor $A_i$. In the same way, these weights $k_i$ defined as an integer multiplier of accelerator factors $A_i$. The weights could be applied equally to the reduction factors $R_j$ being defined as $k_j$, as the presence of a filter with the appropriate absorbances could justly be.

Defined the factors, the rate of exposure to an emission in the range of 380 to 500 nm is defined as follows:

$$I = \text{age} * \sum_{i,j=1}^{n} \frac{k_i A_i}{k_j R_j} \Delta t$$

Where the age is a integer that represents the age of the user, which is proportional to the condition of the blue light (as can be seen in the table, the older person, the higher percentage of absorbance is, except for younger children, where it is necessary a special protection since the eye is not fully formed) and the time differential is defined as the exposure time minus the rest time, where the vision tends to be recovered in a variable way.

This rate is a multiplier of the emissions received, such that the importance of these emissions is directly affected by the age (which is the factor that has more influence in the estimate of the damage to the ocular system), and is a direct function of accelerators factors and effective exposure time as well as inversely proportional to reduction factors, each of these factors being weighted by a specific weight.

Some might think it is not necessary to have a maximum absorbance range and completely block the passage of the short wavelengths between 380-500. However, the total blocking of the blue light produces effects both on the visibility of the screen and on the individual's circadian cycle itself, so it is logical to set a minimum and maximum absorbance range, minimizing such negative effects. In general, there are studies that state that the 25% of light is blue and you can not remove more than 13% of total, this is 7% of blue, according to different variables.

Once emissions received and weighted are set, the invention notifies the user depending on a series of thresholds. Thus, for example, it could be had a bar with three/four degrees of exposure (low, medium, high, danger) so that not only the user will be warned, but the interaction with the emission source, both manually and automatically, is allowed. Thus, if the source is the mobile phone, or computer screen itself, when the high level is reached, the user will be warned and can interact with it, for example by reducing the brightness of the screen, such that when reducing the weight k of this accelerator factor, the rate I will decrease, and the level of risk can be corrected, that is, the emission received multiplied by the rate. Similarly, if the solution is to activate a software filter, the weight of the reduction factor would increase significantly, reducing the rate and, therefore, lowering the level of risk.

In any case, in a particular embodiment, it can be defined that when exceeding certain threshold, the emission source (i.e. the screen) directly turns off, so the invention, applied in mobile phones for games or televisions, or mobile devices could be even used as parental control to prevent abuse of minors.

As indicated, the invention can be implemented on a mobile phone and, in general, any portable electronic device, as glasses of the type Google Glass®. That is, the detector may be on the phone itself, may be a stand-alone device 100 as described in FIG. 1 or any other programmable electronic device.

In a embodiment of the invention, the device detects when the user has the eyes open. The system, once the device is activated, for example, when the accelerometer of the device detects a movement of the same, the system can understand that user is awake and therefore with his/her eyes open. That it is on the outside can also infer, since through the detection of a change in position it is possible to know precisely that said change of position is not compatible with the indoor movement, there are various detection methods of change of position, GPS, triangulation of GSM antennas, detection of WIFI networks, etc.

It is also possible to predict the amount of emissions that someone will receive, such that, for example, a movie may include in its file the total emissions emitted and warn the user when these emissions are excessive in relation to its visual activity, anticipating information and allowing the user to decide if he/she wants to see the content. It is also possible to predict the quantity of emissions, for example on a trip or on a long walk, if the system knows directly or inferring from its behavior the duration of a journey and its average level of emissions, through, weather prediction or through position or any other type of detectors that allow knowing the expected level of emissions, the device or system will assess the level of emissions and recommend to the individual a certain behavior or anticipate what the individual can do.

As indicated, the emission information can be stored remotely, on the server 400, for example.

The system can deduce the activity of radiation exposure by any of the methods that allow knowing the activity of an individual, for example the deduction that the individual is sleeping when the following conditions are met, the phone detects that it is in the residence, for example through the detection of WIFI, and the time matches with that usually the user is sleeping, or for example, the user has set the alarm clock and has connected the mobile phone charger, activity normally related to bedtime. It can also learn of the specific human conduct and actively ask questions when it is unclear if something is happening or not, for example, it detects a change of position and its brightness detector indicates that is accessing low light, because of, for example, the device is in the pocket.

The invention, therefore, is an effective tool for preventive medicine and public health. In addition, given the characteristics of the devices, these can be connected in some embodiments to servers of telemedicine (such as the server 400) to remotely monitor user's visual behavior.

Toxicity Test

In the state of the art the degree of toxicity of the short wavelengths, produced by LED light of different spectral composition, due to the use of an electronic device equipped with this type of displays (LED) on retinal pigment epithelial cells, has not been described.

Figure 4:
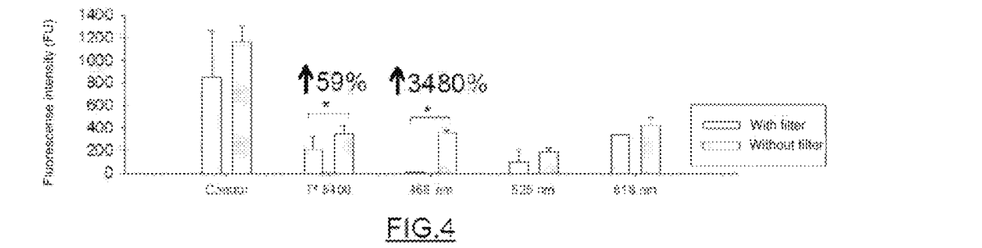
FIG. 4 shows a graph with the LED light effect and the photoprotective effect of a blocking element that selectively absorbs the short wavelengths on the cell viability, indicative of cell survival in human retinal pigment epithelial cells.

The specific objectives of the toxicity test and the provided solution are as follows:

Study the cell viability of the retinal tissue in vitro after exposure to different LEDs that emit radiation of different spectral composition, as shown in FIG. 4.

Figure 5:
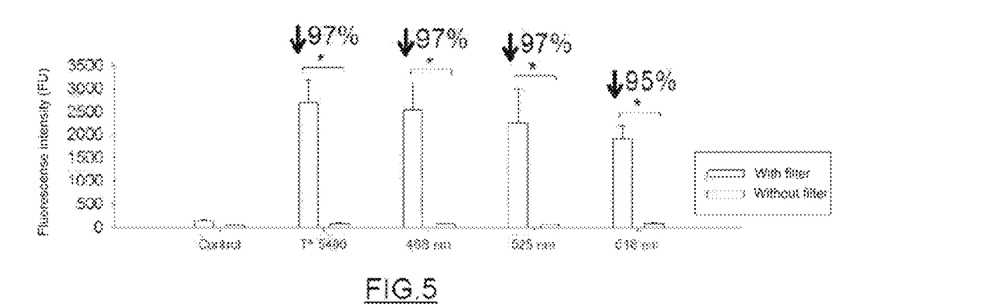
FIG. 5 shows the LED light effect and the photoprotective effect of a blocking element that selectively absorbs the short wavelengths on the activation of the human histone H2AX, indicative of DNA damage in human retinal pigment epithelial cells.

Assess the DNA damage of the retinal tissue in vitro after exposure to different LEDs that emit radiation of different spectral composition, as shown in FIG. 5.

Figure 6:
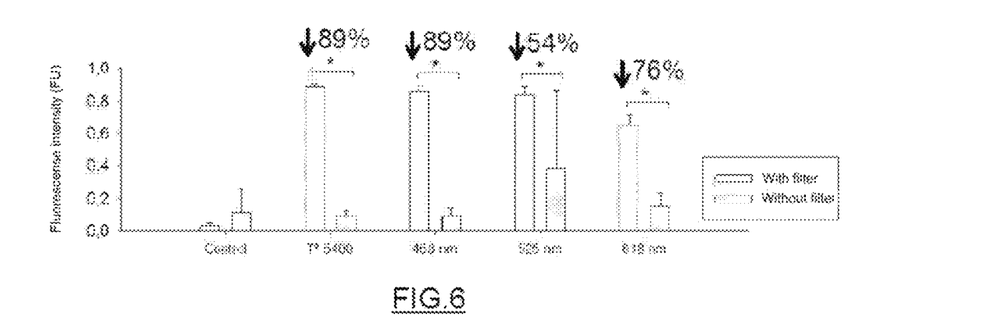
FIG. 6 shows the LED light effect and photoprotective effect of a blocking element that selectively absorbs the short wavelengths on the activation of the caspase-3, -7, indicative of apoptosis in human retinal pigment epithelial cells.

Determine the apoptosis of the retinal tissue in vitro after exposure to different LEDs that emit radiation of different spectral composition, as shown in FIG. 6.

Following the assessment and determination of toxicity, the solutions proposed in the present invention are assessed.

TABLE 2

| Reagent/Equipment and Catalogue and lot Numbers | Supplier |
| --- | --- |
| Human Retinal Pigment Epithelial cells # P10873- | ScienceII |
| Poly-L-lysina # P4707 Lot N° BCBC0503 | Sigma Aldrich |
| Epithelial cell medium #P60106 | ScienceII |
| TMRM #P668 | Invitrogen |
| CM-H2DCPDA #C6827 | Invitrogen |
| Rabbit anti caspase3 antibody # 9661 Lot N° P42574 | Cell Signalling |
| Mouse anti H2AX antibody #ab22551 Lot N° 820115 | Abcum |
| Goal anti-rabbit antibody Alexa 594 # A11012 Lot N° 695244 | Invitrogen |
| Goal anti-mouse antibody Alexa 633 # A21050 Lot N° 690316 | Invitrogen |
| Nowell, black clear Imaging Plate #353219 | Becton Dickinson |
| Sovine serum albumin #A2153 | Sigma |
| Paraformaldehyde #16005 | Sigma |
| BD Pathway 855 | Becton Dickinson |
| Hydrogen Peroxide Sol 3% Lot D401A | |

Figure 3:
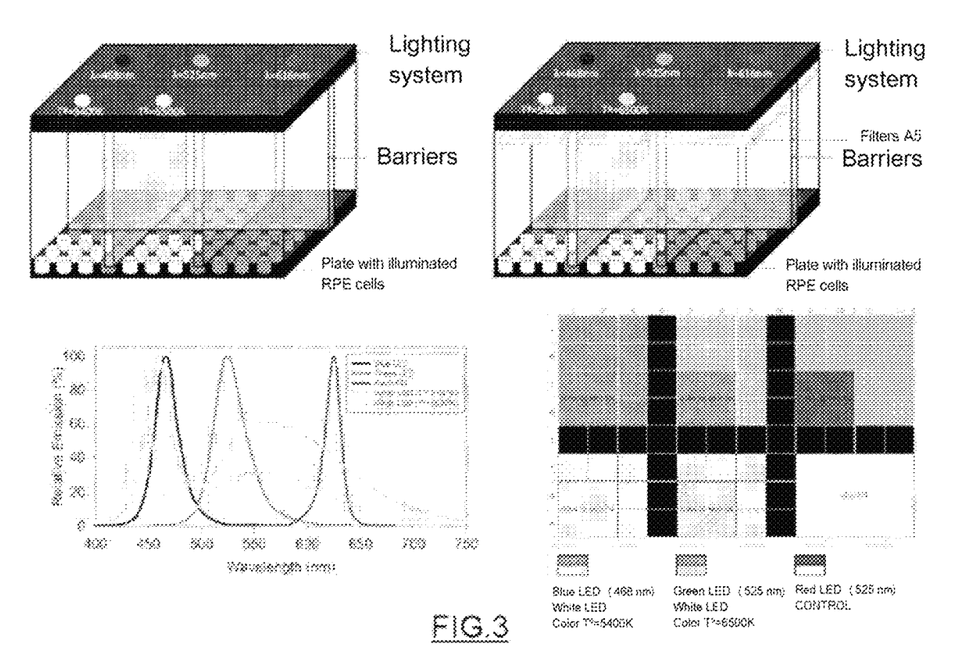
FIG. 3 shows a view of the LED-type light source used for the example described by the present invention. A. Schematic representation of the lighting device without and with the blocking element of short wavelengths used. B. Spectral emission curves of each of the used LEDs. C. Design of the well plate where the cells were seeded.

In table 2, a summary of the reagents, equipment and supplied material used in the study is found. On the other hand, a lighting device has been designed comprising five differentiated lighting zones separated off from each other by discriminating barriers of a white material. Each one of the zones contains a LED producing light of irradiance 5 mW/cm$^2$ but emitting light with different spectral composition:

Blue LED (468 nm)
Green LED (525 nm)
Red LED (616 nm)
White LED; Color T°=5400° K FIG. 3 represents schematically the lighting device used and the spectral emission curves of each of the LEDs. This device was placed on the culture plate, and the cells were exposed to LED light only for 3 light-dark cycles (12 hours/12 hours) with and without the interposition of the blocking element of short wavelengths. As shown, there is a zone not illuminated by LEDs where the cells not exposed to light which were used as negative control are placed.

In this non-limitative, particular embodiment, the blocking element is defined as a blocking element of short wavelengths consisting of a substrate with a yellow pigment evenly distributed on its surface and, in that said pigment has an optical density such that it allows the selective absorption of short wavelengths between 380 nm and 500 nm in a range between 1 and 99%. More specifically, it is a film or multilayer film, where one of them is pigmented.

Cell Culture and Plate Design

The retinal pigment epithelial cells (RPE) were thawed following the supplier's instructions, in 'Epithelial cell culture medium', supplemented with fetal bovine serum (FBS) and growth factors. At 72 hours and once the culture reaches the confluence, the cells were raised with trypsin-EDTA and were seeded at a density of 5000 cells/well in a 96-well plate previously treated with poly-lysine. The culture was kept for 24 hours after which the medium was replaced by fresh medium (300 µl/well). This procedure was repeated each of the days in which the experiment was carried out to avoid evaporations by the heat produced by the lamps. The plate with the lighting device was placed within the incubator at 37° C. in an atmosphere of 5% $CO_2$.

The toxicity experiment was conducted after the cells were incubated in the presence of light of different spectral characteristics for 3 exposure/rest cycles of 12 hours per cycle.

The samples were washed with PBS and fixed with 4% paraformaldehyde for 15 minutes. After fixation, the cells were permeated with 0.3% Triton for 10 minutes. Once the samples were permeated, they were blocked with 5% BSA and the anti-caspase and anti-H2AX antibodies dissolved in 2.5% PBS+BSA were then added at a concentration of 1:400 for the determination of apoptosis and DNA damage respectively.

After an hour of incubation, the samples were washed with PBS, and secondary antibodies, Alexa 594 and Alexa 633, were added at the same concentration as the primary antibody and incubated for 30 minutes. After incubation, the samples were washed and the signal was read in the BD Pathway 855 fluorescence microscope. For the activation of caspases, images were captured at 633 nm of emission and for H2AX at 594 nm.

Statistical Analysis

Each experiment was repeated at least twice. The values are given as mean±standard deviation. The data were analyzed by statistical unpaired Student's t-test using the statistical software Statgraphics version Centurion XVI.I (USA). P-values of less than 0.05 were considered to be significant.

Results. Cell Viability

After a period of 3 light exposure cycles to for 12 hours, alternating with 3 recovery cycles for a further 12 hours, the nuclei of the primary human retinal pigment epithelial cells were DAPI-stained to count the number of cells per well.

The non-irradiated cells grew well in the wells, but irradiation with monochromatic LED light inhibited cell growth. Blue light (468 nm) produced a very significant reduction in the number of cells, although there was also an observable phototoxic effect for green light (525 nm). In the case of white light (T°=5400° K) no statistically significant differences were observed.

With the presence of the blocking element of short wavelengths, an increase of cell viability was observed, mainly in cells exposed to white light (T°=5400° K) and light blue (468 nm) as shown in the table 3.

TABLE 3

| Cell viability | Control | white LED (T° = 5400° K) | Blue LED (468 nm) | Green LED (525 nm) | Red LED (616 nm) |
| --- | --- | --- | --- | --- | --- |
| Without blocking element (FU) | 855 ± 403 | 217 ± 108 | 10 ± 2 | 99 ± 114 | 339 ± 1 |
| With blocking element (FU) | 1156 ± 156 | 346 ± 71 | 358 ± 20 | 188 ± 43 | 420 ± 69 |
| p-value | 0.212 | 0.047* | 0.000* | 0.102 | 0.096 |
| Increase (%) | — | 59 | 3480 | — | — |

In FIG. 4, the LED light effect and the photoprotective effect of a blocking element that selectively absorbs the short wavelengths on the cell viability in human retinal pigment epithelial cells can be seen. FU means fluorescence unit.

Results: DNA Damage

To examine whether the radiation had some effect on the integrity of cellular DNA, cells were marked using H2AX antibody.

H2AX is a variant of the histone H2A that is involved in DNA repair, i.e. when there is damage in nuclear DNA. When the double-stranded DNA break occurs, H2AX histone is rapidly phosphorylated on serine 139 by kinase ATM and becomes Gamma-H2AFX.

This phosphorylation step can extend to several thousands of nucleosomes from the site of the double-strand break and can mark the surrounding chromatin in the recruitment of the proteins necessary for damage signaling and DNA repair. As part of post-translational modifications of apoptosis, caused by severe DNA damage, a high expression of phosphorylated H2AX is considered as an accurate indicator of apoptosis.

The results of experiments showed that anti-H2AX antibody recognizes sites of phosphorylated histones after irradiation with LED light indicating an activation of DNA repair mechanisms.

By interposing the blocking element of the short wavelengths, a significant decrease in activation of histone H2AX, indicative of less DNA damage, was observed. This decrease was 97% for white (T°=5400° K), blue (468 nm), and green (525 nm) LED light, and 95% in cells exposed to red LED light, as seen in table 4.

TABLE 4

| Activation of H2AX | Control | White LED (T° = 5400° K) | Blue LED (468 nm) | Green LED (525 nm) | Red LED (616 nm) |
|---|---|---|---|---|---|
| Without blocking element (FU) | 131 ± 41 | 2697 ± 493 | 2537 ± 589 | 2258 ± 738 | 1920 ± 286 |
| With blocking element (FU) | 47 ± 1 | 83 ± 20 | 76 ± 7 | 63 ± 10 | 91 ± 15 |
| p-value | 0.024* | 0.000* | 0.002* | 0.001* | 0.000* |
| Decrease (%) | — | 97% | 97% | 97% | 95% |

In FIG. 5, the LED light effect and the photoprotective effect of a blocking element that selectively absorbs the short wavelengths on the activation of histone H2AX in human retinal pigment epithelial cells, is shown. FU means fluorescence unit.

Results: Apoptosis

The activation of caspase-3 and -7 was determined, since these enzymes are involved in the regulation and execution of apoptosis. The cells were marked using the anti-caspase antibody. Irradiation with LED light in the cells caused an increase in the percentage of apoptotic cells in the culture. The caspase activation is observed as a pinkish color around the blue-stained nucleus (DAPI). The interposition of the blocking element of short wavelengths induced a significant decrease in caspase activation, indicative of apoptosis in cells exposed to the different LED light sources. This decrease was 89% for white (T°=5400° K) and blue (468 nm) lights, 54% for green light (525 nm), and 76% for red light, as shown in table 5.

TABLE 5

| Activation of caspases | Control | White LED (T° = 5400° K) | Blue LED (468 nm) | Green LED (525 nm) | Red LED (616 nm) |
|---|---|---|---|---|---|
| Without blocking element (FU) | 0.037 ± 0.02 | 0.888 ± 0.02 | 0.861 ± 0.03 | 0.839 ± 0.05 | 0.655 ± 0.07 |
| With blocking element (FU) | 0.114 ± 0.15 | 0.094 ± 0.03 | 0.094 ± 0.05 | 0.386 ± 0.48 | 0.155 ± 0.08 |
| p-value | 0.541 | 0.000* | 0.000* | 0.312 | 0.006* |
| Reduction (%) | — | 89% | 89% | 54% | 76% |

In FIG. 6, the LED light effect and photoprotective effect of a blocking element that selectively absorbs the short wavelengths on the activation of the caspase-3, -7 in human retinal pigment epithelial cells, is shown. FU means fluorescence unit.

Following an analysis of the problem and an example of solution, the light, especially that of smaller wavelengths, in 3 cycles of 12 hours of exposure alternating with 12 hours of recovery, affects the growth of the human retinal pigment epithelial cells. An increase in the number of cells expressing the histone H2AX (DNA damage) y caspase-3 and -7 (apoptosis) occurs.

In all cases the blocking element that selectively absorbs the short wavelengths exerts a protective effect against the damaging effects of light on the human retinal pigment epithelial cells.

The invention claimed is:

1. A method for detection and quantification of blue and violet light of the visible spectrum of a light source comprising the steps of:

detecting a light emission of the light source;

establishing a weighted accelerator factor of the light emission of the light source within a wavelength range between 380 nm and 500 nm, wherein said weighted accelerator factor is at least one of:

a size of the light source; a separation distance from the light source to a user being exposed to the light source; an ambient lighting during an exposure time; or an ocular disease of the user being exposed to the light source;

establishing a weighted reduction factor of the light emission of the light source within a wavelength range between 380 nm and 500 nm, wherein said weighted reduction factor comprises, at least, a filter with an absorbance wavelength range between 380 nm and 500 nm;

establishing the age of the user being exposed to the light source;

calculating the effective exposure time to the light emission of the light source as the differential time between the total exposure time to the light emission of the light source minus the rest time of the user being exposed to the light source;

calculating a rate of exposure to the light emission of the light source within a wavelength range between 380 nm and 500 nm defined as follows:

$$I = \text{age} * \sum_{i,j=1}^{n} \frac{k_i A_i}{k_j R_j} \Delta t$$

wherein age is an integer that represents the age of the user being exposed to the light source; a weight $k_i$ is an integer multiplier of accelerator factors $A_i$; a weight $k_j$ is an integer multiplier of the reduction factors $R_j$; and $\Delta t$ represents the effective exposure time to the light emission of the light source;

calculating a user's received emission of the light source within the wavelength range between 380 nm and 500 nm defined as a product of the rate of exposure multiplied by the light emission of the light source; and determining if the user's received emission of the light source, based upon the calculation, exceeds a defined threshold of light emission of the light source within the wavelength range between 380 nm and 500 nm.

2. The method of claim 1, further comprises at least one of warning the user when the threshold has been exceeded and turning off the light source when the threshold has been exceeded.

3. The method of claim 1, wherein the light source is a LED-type display viewed by the user.

4. A method for detection and quantification of blue and violet light of the visible spectrum of a light source comprising the steps of:
   detecting a light emission of the light source;
   establishing a weighted accelerator factor of the light emission of the light source within a wavelength range between 380 nm and 500 nm, wherein said weighted accelerator factor is at least one of:
   a size of the light source; a separation distance from the light source to a user being exposed to the light source; an ambient lighting during an exposure time; or an ocular disease of the user being exposed to the light source;
   establishing a weighted reduction factor of the light emission of the light source within a wavelength range between 380 nm and 500 nm, wherein said weighted reduction factor comprises, at least, a filter with an absorbance wavelength range between 380 nm and 500 nm;
   establishing the age of the user being exposed to the light source;
   calculating the effective exposure time to the light emission of the light source as the differential time between the total exposure time to the light emission of the light source minus the rest time of the user being exposed to the light source;
   calculating a rate of exposure to the light emission of the light source within a wavelength range between 380 nm and 500 nm defined as follows:

$$I = \text{age} * \sum_{i,j=1}^{n} \frac{k_i A_i}{k_j R_j} \Delta t$$

wherein age is an integer that represents the age of the user being exposed to the light source; a weight $k_i$ is an integer multiplier of accelerator factors $A_i$; a weight $k_j$ is an integer multiplier of the reduction factors $R_j$; and $\Delta t$ represents the effective exposure time to the light emission of the light source;
   calculating a user's received emission of the light source within the wavelength range between 380 nm and 500 nm defined as a product of the rate of exposure multiplied by the light emission of the light source; and
   determining if the user's received emission of the light source, based upon the calculation, exceeds at least one of a series of thresholds of light emission of the light source within the wavelength range between 380 nm and 500 nm.

5. The method of claim 4, further comprises at least one of warning when at least one of the series of thresholds has been exceeded and turning off the light source when at least one of the series of thresholds has been exceeded.

6. The method of claim 4, wherein the light source is a LED-type display viewed by the user.

7. A portable electronic device for detection and quantification of blue and violet light of the visible spectrum of a light source comprising:
   a light detector in the range of the visible spectrum;
   a signal conditioning circuit connected to the detector;
   an analog-to-digital converter;
   a processor; and
   a non-transitory program that is stored in a memory of the processor and is configured to be executed by the processor, the non-transitory program including instructions configured to cause the processor to:
   detect a light emission of the light source;
   establishing a weighted accelerator factor of the light emission of the light source within a wavelength range between 380 nm and 500 nm, wherein said weighted accelerator factor is at least one of:
   a size of the light source; a separation distance from the light source to a user being exposed to the light source; an ambient lighting during an exposure time; or an ocular disease of the user being exposed to the light source;
   establishing a weighted reduction factor of the light emission of the light source within a wavelength range between 380 nm and 500 nm, wherein said weighted reduction factor comprises, at least, a filter with an absorbance wavelength range between 380 nm and 500 nm;
   establishing the age of the user being exposed to the light source;
   calculating the effective exposure time to the light emission of the light source as the differential time between the total exposure time to the light emission of the light source minus the rest time of the user being exposed to the light source;
   calculating a rate of exposure to the light emission of the light source within a wavelength range between 380 nm and 500 nm defined as follows:

$$I = \text{age} * \sum_{i,j=1}^{n} \frac{k_i A_i}{k_j R_j} \Delta t$$

wherein age is an integer that represents the age of the user being exposed to the light source; a weight $k_i$ is an integer multiplier of accelerator factors $A_i$; a weight $k_j$ is an integer multiplier of the reduction factors $R_j$; and $\Delta t$ represents the effective exposure time to the light emission of the light source;
   calculating a user's received emission of the light source within the wavelength range between 380 nm and 500 nm defined as a product of the rate of exposure multiplied by the light emission of the light source; and
   determining if the user's received emission of the light source, based upon the calculation, exceeds a defined threshold of light emission of the light source within the wavelength range between 380 nm and 500 nm.

8. The device according to claim 7, further comprising a Bluetooth transmitter.

9. The device according to claim 7, further comprising a signal light.

10. The device according to claim 7, further comprising a GPS locator.

11. A portable electronic device for detection and quantification of blue and violet light of the visible spectrum of a light source comprising:

a light detector in the range of the visible spectrum;
a signal conditioning circuit connected to the detector;
an analog-to-digital converter;
a processor; and
a non-transitory program that is stored in the memory of a processor and is configured to be executed by the processor, the non-transitory program including instructions configured to cause the processor to:
detect a light emission of the light source;
establishing a weighted accelerator factor of the light emission of the light source within a wavelength range between 380 nm and 500 nm, wherein said weighted accelerator factor is at least one of:
a size of the light source; a separation distance from the light source to a user being exposed to the light source; an ambient lighting during an exposure time; or an ocular disease of the user being exposed to the light source;
establishing a weighted reduction factor of the light emission of the light source within a wavelength range between 380 nm and 500 nm, wherein said weighted reduction factor comprises, at least, a filter with an absorbance wavelength range between 380 nm and 500 nm;
establishing the age of the user being exposed to the light source;
calculating the effective exposure time to the light emission of the light source as the differential time between the total exposure time to the light emission of the light source minus the rest time of the user being exposed to the light source;
calculating a rate of exposure to the light emission of the light source within a wavelength range between 380 nm and 500 nm defined as follows:

$$I = \text{age} * \sum_{i,j=1}^{n} \frac{k_i A_i}{k_j R_j} \Delta t$$

wherein age is an integer that represents the age of the user being exposed to the light source; a weight $k_i$ is an integer multiplier of accelerator factors $A_i$; a weight $k_j$ is an integer multiplier of the reduction factors $R_j$; and $\Delta t$ represents the effective exposure time to the light emission of the light source;
calculating a user's received emission of the light source within the wavelength range between 380 nm and 500 nm defined as a product of the rate of exposure multiplied by the light emission of the light source; and
determining if the user's received emission of the light source, based upon the calculation, exceeds at least one of a series of thresholds of light emission of the light source within the wavelength range between 380 nm and 500 nm.

12. The device according to claim 11, further comprising a Bluetooth transmitter.

13. The device according to claim 11, further comprising a signal light.

14. The device according to claim 11, further comprising a GPS locator.

15. A computer system for detection and quantification of the blue and violet light of visible spectrum from a light source comprising:
a display connected to a display controller;
a camera;
a processor; and
a non-transitory program that is stored in a memory of the processor and is configured to be executed by the processor, the non-transitory program including instructions configured to cause the processor to:
detect a light emission of the light source;
establishing a weighted accelerator factor of the light emission of the light source within a wavelength range between 380 nm and 500 nm, wherein said weighted accelerator factor is at least one of:
a size of the light source; a separation distance from the light source to a user being exposed to the light source; an ambient lighting during an exposure time; or an ocular disease of the user being exposed to the light source;
establishing a weighted reduction factor of the light emission of the light source within a wavelength range between 380 nm and 500 nm, wherein said weighted reduction factor comprises, at least, a filter with an absorbance wavelength range between 380 nm and 500 nm;
establishing the age of the user being exposed to the light source;
calculating the effective exposure time to the light emission of the light source as the differential time between the total exposure time to the light emission of the light source minus the rest time of the user being exposed to the light source;
calculating a rate of exposure to the light emission of the light source within a wavelength range between 380 nm and 500 nm defined as follows:

$$I = \text{age} * \sum_{i,j=1}^{n} \frac{k_i A_i}{k_j R_j} \Delta t$$

wherein age is an integer that represents the age of the user being exposed to the light source; a weight $k_i$ is an integer multiplier of accelerator factors $A_i$; a weight $k_j$ is an integer multiplier of the reduction factors $R_j$; and $\Delta t$ represents the effective exposure time to the light emission of the light source;
calculating a user's received emission of the light source within the wavelength range between 380 nm and 500 nm defined as a product of the rate of exposure multiplied by the light emission of the light source; and
determining if the user's received emission of the light source, based upon the calculation, exceeds a defined threshold of light emission of the light source within the wavelength range between 380 nm and 500 nm.

16. The system according to claim 15, wherein the display is a LED-type display.

17. A computer system for detection and quantification of the blue and violet light of visible spectrum from a light source comprising:
a display connected to a display controller;
a camera;
a processor; and
a non-transitory program that is stored in a memory of the processor and is configured to be executed by the processor, the non-transitory program including instructions configured to cause the processor to:
detect a light emission of the light source;
establishing a weighted accelerator factor of the light emission of the light source within a wavelength range between 380 nm and 500 nm, wherein said weighted accelerator factor is at least one of:
a size of the light source; a separation distance from the light source to a user being exposed to the light source; an ambient lighting during an exposure time; or an ocular disease of the user being exposed to the light source;
establishing a weighted reduction factor of the light emission of the light source within a wavelength range between 380 nm and 500 nm, wherein said weighted reduction factor comprises, at least, a filter with an absorbance wavelength range between 380 nm and 500 nm;
establishing the age of the user being exposed to the light source;
calculating the effective exposure time to the light emission of the light source as the differential time between the total exposure time to the light emission of the light source minus the rest time of the user being exposed to the light source;
calculating a rate of exposure to the light emission of the light source within a wavelength range between 380 nm and 500 nm defined as follows:

$$I = \text{age} * \sum_{i,j=1}^{n} \frac{k_i A_i}{k_j R_j} \Delta t$$

wherein age is an integer that represents the age of the user being exposed to the light source; a weight $k_i$ is an integer multiplier of accelerator factors $A_i$; a weight $k_j$ is an integer multiplier of the reduction factors $R_j$; and $\Delta t$ represents the effective exposure time to the light emission of the light source;

calculating a user's received emission of the light source within the wavelength range between 380 nm and 500 nm defined as a product of the rate of exposure multiplied by the light emission of the light source; and
determining if the user's received emission of the light source, based upon the calculation, exceeds at least one of a series of thresholds of light emission of the light source within the wavelength range between 380 nm and 500 nm.

18. The system according to claim 17, wherein the display is a LED-type.

19. A non-transitory computer program product with instructions configured for execution by one or more processors that, when running, carry out the method of claim 1.

20. A non-transitory computer program product with instructions configured for execution by one or more processors that, when running, carry out the method of claim 4.

21. The device according to claim 7, wherein the processor is further configured to at least one of warn the user when the threshold has been exceeded and turn off the light source when the threshold has been exceeded.

22. The device according to claim 11, wherein the processor is further configured to at least one of warn the user when at least one of the series of thresholds has been exceeded and turn off the light source when at least one of the series of thresholds has been exceeded.

23. The system according to claim 15, wherein the processor is further configured to at least one of warn the user when the threshold has been exceeded and turn off the light source when the threshold has been exceeded.

24. The system according to claim 17, wherein the processor is further configured to at least one of warn the user when at least one of the series of thresholds has been exceeded and turn off the light source when at least one of the series of thresholds has been exceeded.

* * * * *